United States Patent
Kim et al.

(10) Patent No.: US 11,566,056 B2
(45) Date of Patent: Jan. 31, 2023

(54) PEPTIDE AND USE THEREOF FOR TREATMENT OF DISEASE OF BRAIN AND NERVOUS SYSTEM

(71) Applicants: SYLUS CO., LTD, Jeollabuk-do (KR); Daegu Gyeongbuk Institute of Science and Technology, Daegu (KR)

(72) Inventors: So Yeon Kim, Daegu (KR); Che Il Moon, Daegu (KR)

(73) Assignees: SYLUS CO., LTD, Jeollabuk-do (KR); Daegu Gyeongbuk Institute of Science and Technology, Daegu (KR)

( * ) Notice: Subject to any disclaimer, the term of this patent is extended or adjusted under 35 U.S.C. 154(b) by 0 days.

(21) Appl. No.: 17/330,479

(22) Filed: May 26, 2021

(65) Prior Publication Data
US 2021/0371484 A1    Dec. 2, 2021

(30) Foreign Application Priority Data

May 26, 2020  (KR) ................. 10-2020-0063279
May 14, 2021  (KR) ................. 10-2021-0062815

(51) Int. Cl.
*C07K 14/505*  (2006.01)
*A61P 25/28*   (2006.01)
*A61K 38/00*   (2006.01)

(52) U.S. Cl.
CPC .......... *C07K 14/505* (2013.01); *A61P 25/28* (2018.01); *A61K 38/00* (2013.01)

(58) Field of Classification Search
CPC ........ C07K 14/505; A61P 25/28; A61K 38/00
See application file for complete search history.

(56) References Cited

U.S. PATENT DOCUMENTS

2020/0407410 A1   12/2020  Moon et al.

FOREIGN PATENT DOCUMENTS

| KR | 20180099546 | 9/2018 |
| WO | 2006120030  | 11/2006 |
| WO | 2009152944  | 12/2009 |
| WO | 2018155997  | 8/2018 |
| WO | 2020045886  | 3/2020 |

OTHER PUBLICATIONS

"Search Report of Europe Counterpart Application", dated Oct. 22, 2021, p. 1-p. 10.
Bo Wang et al., "Beneficial Effect of Erythropoietin Short Peptide on Acute Traumatic Brain Injury," Neurotherapeutics, Dec. 2015, pp. 418-427.

*Primary Examiner* — Amber D Steele
(74) *Attorney, Agent, or Firm* — JCIPRNET

(57) ABSTRACT

Peptides are easy to pass through a tissue-blood barrier, have excellent physiological activity in the protective activity of cells, and have an economic advantage due to low production costs. In addition, since there is no side effect of cell proliferation, a pharmaceutical composition containing a peptide of an aspect as an active ingredient can be usefully used in the treatment or prevention of neurological disorders and degenerative brain diseases.

6 Claims, 15 Drawing Sheets

Specification includes a Sequence Listing.

FIG. 1B

| Peptides | | Amino acid sequence |
|---|---|---|
| | | 91                                                      113 |
| | Helix C of EPO | ...L Q L H V D K A V S G L R S L T T L L R A L G... |
| hydrophobic | SY-1 | L Q L H V L K A V S G L R T L T T L L R A L G |
| | SY-2 | L Q L H V L K A V S G L R T L T M I R R A L G |
| | SY-3 | L Q L H V L K A V A G L R T L T M I R R A L A |

PEPTIDE AND USE THEREOF FOR TREATMENT OF DISEASE OF BRAIN AND NERVOUS SYSTEM

CROSS-REFERENCE TO RELATED APPLICATIONS

This application is based on and claims priority under 35 USC § 119 to Korean Patent Application Nos. 10-2020-0063279, filed on May 26, 2020, and 10-2021-0062815, filed on May 14, 2021, in the Korean Intellectual Property Office, the disclosures of which are incorporated by reference herein in their entirety.

BACKGROUND

1. Field

Embodiments of the present disclosure relate to a novel peptide from which cell-proliferation side effects have been removed, and a pharmaceutical composition for preventing or treating diseases of brain and nervous system, including the peptide.

2. Description of the Related Art

The nervous system is a complex and sophisticated organ that regulates and controls the activities of our body, and can be largely classified into the central nervous system and the peripheral nervous system. The central nervous system includes the brain (cerebrum, cerebellum, brainstem) and spinal cord, and the peripheral nervous system includes all nervous systems except the central nervous system.

Diseases of the nervous system include stroke (ischemic, hemorrhagic), nerve cell damage, degenerative diseases (Alzheimer's disease, dementia with Lewy bodies, Parkinson's disease, chorea, spinal cerebellar ataxia, etc.), tumors, structural defects (arteriovenous malformations, aneurysms, neuronal development disorders, etc.), functional disorders (epilepsy, headache, sleep disorders, neuralgia, dizziness, etc.), metabolic diseases (chronic renal failure, diabetes, etc.), etc. Neurodegenerative disease are gradually increasing in incidence, from among diseases occurring in the nervous system, as the average life span of humans increases. Neurodegenerative diseases are such a disease that causes dysfunction and various symptoms, as degenerative changes appear in nerve cells of the central nervous system.

In particular, strokes include cerebral infarction caused by blockage of blood vessels to the brain, cerebral hemorrhage caused by rupture of blood vessels, and cerebral ischemia caused by decreased cerebral blood flow, all of which may cause neurological diseases or degenerative nerve damage. In addition, even without there is no a special disease, a stroke may occur, and brain damage may occur.

Stroke, Alzheimer's disease, Parkinson's disease, Lou Gehrig's disease, and Huntington's disease, which are degenerative neurological diseases, have not been fully identified despite a lot of efforts, so products targeting the neurotransmitter process are released and sold mainly to relieve symptoms. Antiplatelet drugs are the most important drugs in the secondary stroke prevention treatment. Since antiplatelet drugs lower the function of platelets, it is difficult to proceed hemostasis, which is a common disadvantage. That is, antiplatelet drugs have side effects related to bleeding. As an anticoagulant, only warfarin (coumadin), which is a vitamin K antagonist, has long been used. Many patients with cerebral infarction complain of cognitive dysfunction or impaired behavioral and emotional control after the onset of cerebral infarction.

Accordingly, the inventors of the present application have invented a peptide that does not induce cell proliferation and exhibits the effects of neuronal cell protection and brain protection. In addition, they produced a peptide that easily passes the tissue vascular barrier existing in the body, thereby completing the present disclosure.

SUMMARY

An aspect provides a peptide including any one amino acid sequence selected from SEQ ID NOs: 1 to 3.

Another aspect is to provide a pharmaceutical composition for preventing or treating diseases of brain and nervous system, containing, as an active ingredient, the peptide, at least one polynucleotide encoding the peptide, a vector containing the polynucleotide, or a host cell containing the vector.

Additional aspects will be set forth in part in the description which follows and, in part, will be apparent from the description, or may be learned by practice of the presented embodiments of the disclosure.

An aspect provides a peptide including any one amino acid sequence selected from SEQ ID NOs: 1 to 3.

The "peptide" refers to a polymer consisting of two or more amino acids linked by an amide bond (or a peptide bond), and specifically, the peptide may consist of any one amino acid sequence selected from SEQ ID NOs: 1 to 3.

In an embodiment, the peptide may include a peptide having an amino acid sequence selected from SEQ ID NOs: 1 to 3 and a fragment thereof, and for use as the peptide, of these peptides and fragments thereof, one or more amino acids, two or more amino acids, three or more amino acids, four or more amino acids, five or more amino acids, six or more amino acids, or seven or more amino acids may be modified.

In addition, to obtain better chemical stability, enhanced pharmacological properties (half-life, absorption, titer, potency, etc.), altered specificity (e.g., a broad spectrum of biological activity), and reduced antigenicity, a protecting group may be bonded to the N- or C-terminus of the peptides. In an embodiment, the protecting group may be an acetyl group, a fluorenyl methoxycarbonyl group, a formyl group, a palmitoyl group, a myristyl group, a stearyl group, or polyethylene glycol (PEG), and any component that improves the modification of the peptide, especially the stability of the peptide may be included without limitation. In an embodiment, the N-terminus of the peptide may be combined with any one protecting group selected from an acetyl group, a fluorenylmethoxycarbonyl group, a formyl group, a palmitoyl group, a myristyl group, stearyl group, and polyethylene glycol (PEG); and/or the C-terminus of the peptide may be combined with any one protecting group selected from an amino group (—NH$_2$), and an azide (—NHNH$_2$).

The "stability" may refer to not only in vivo stability in which the peptide of the present disclosure is protected from attack by protein cleavage enzymes in vivo, but also storage stability (for example, room temperature storage stability).

In addition, the peptide may additionally include a targeting sequence, a tag, and an amino acid sequence prepared for a specific purpose for a labeled residue.

In an embodiment, the change in the amino acid corresponds to a property that causes the physicochemical properties of the peptide to be altered. For example, the change in the amino acid, such as improving the thermal stability of the peptide, altering the substrate specificity, changing the optimal pH, and the like, may be performed.

The term "amino acid" as used herein includes the 22 standard amino acids that are naturally incorporated as a peptide, as well as D-isomers and modified amino acids thereof.

Accordingly, in an aspect of the present disclosure, the peptide may be a peptide containing D-amino acid. Meanwhile, in another aspect of the present disclosure, the peptide may include a non-standard amino acid that is subjected to post-translational modification. Examples of post-translational modifications include phosphorylation, glycosylation, acylation (e.g., acetylation, myristoylation, and palmitoylation), alkylation, carboxylation, hydroxylation, glycation, biotinylation, ubiquitinylation, changes in chemical properties (e.g., beta-removal deimidation, or deamidation), and structural changes (e.g., formation of disulfide bridges). Examples of post-translational modifications include changes in amino acids, such as changes in amino groups, carboxyl groups, or side chains, caused by chemical reactions occurring in the process of bonding with crosslinkers to form peptide conjugates.

The peptides exhibit cytoprotective activity and are characterized by no side effects of cell proliferation.

The peptide may bind to an erythropoietin (EPO) receptor and form an alpha helix structure. In addition, the binding force of the receptor may have a KD value of 0.6 mM to 3.0 mM. For example, the binding force of the receptor may have a KD value of 0.8 mM to 2.8 mM, 0.9 mM to 2.6 mM, 1 mM to 2.5 mM, or 1.1 mM to 2.4 mM.

The peptide of an embodiment may bind to target region 1 (site 1) or target region 2 (site 2) of the erythropoietin receptor.

There are two target regions in the erythropoietin receptor (EPOR), through which a conjugate with erythropoietin (EPO) may be formed. It is known by the prior art that, from among the two binding target regions, target region 1 (site 1) has a strong binding (KD=up to 1 nM) and target region 2 (site 2) has a weak binding (KD=up to 1 μM). The target region targeted according to the present disclosure is a weak binding site, and the weak binding between the erythropoietin receptor and the peptide of the present disclosure makes it possible to prevent side effects (proliferation) induced when erythropoietin binds to the receptor thereof. Arg103, Ser104, Leu105, Leu108, and Arg110 are known as important amino acid sequences of the erythropoietin receptor, and the target region is set based on the sequence of erythropoietin that directly binds to these sites. Specifically, the binding site of the peptide may be $91^{st}$ to $113^{th}$ amino acids of the amino acid sequences of human erythropoietin, which may mean a region targeted by the peptide.

According to an embodiment, the inventors of the present application synthesized peptides from some target regions of natural erythropoietin according to a known solid phase synthesis technique, and confirmed specific properties of each peptide.

The peptide may exhibit cytoprotective activity. In an embodiment, the peptide may protect cells that are placed in a stressful situation or a hypoxic environment. The stress situation may be cell aging or an increase in reactive oxygen. The peptide may reduce the concentration of reactive oxygen species (ROS). In an embodiment, the peptide may have the effect of lowering the degree of mitochondrial activity under high cellular stress.

In an embodiment, the cells may be nerve cells or brain cells. The peptide may have the effect of protecting nerve cells or brain cells. In an embodiment, the peptide may have the effect of protecting nerve cells or brain cells damaged by, for example, cerebral hemorrhage, or alleviate the damage. In an embodiment, the peptide may have an amino acid sequence of SEQ ID NO: 2 or 3.

In an embodiment, the peptide may have no cell-proliferation side effects. In an embodiment, the cell-proliferation side effects may be small compared to when the experimental group administered with erythropoietin was used as a control group. Unlike erythropoietin, which has a cell-protective effect and cell-proliferation side effects, the peptide according to an aspect may have a high cytoprotective effect and a small cell proliferation side effect. The cell proliferation side effect may refer to an increase in red blood cells or an increase in platelet activity.

Therefore, the peptide of the present disclosure may bind to erythropoietin receptors, inhibit cell death, and have no side effects of cell proliferation, so that it can be usefully used in the prevention or treatment of diseases of brain and nervous system.

An aspect provides a pharmaceutical composition for preventing or treating diseases of brain and nervous system, containing, as an active ingredient, a peptide including any one amino acid sequence selected from SEQ ID NOs: 1 to 3, at least one polynucleotide encoding the peptide, a vector containing the polynucleotide, or a host cell containing the vector.

The peptide and sequence numbers are as described above.

The composition may exhibit cytoprotective activity and may have no side effects of cell proliferation.

The diseases of brain and nervous system include cerebral palsy, brain injury, traumatic brain injury, ischemic brain injury, concussion, brain bruise, cerebral infarction, cerebral hemorrhage, Parkinson's disease, Alzheimer's disease, Huntington's disease, stroke, dementia, Lou Gehrig's disease, Pick's disease, Creutzfeld-Jakob disease, amyotrophic axonal sclerosis, primary axonal sclerosis, degenerative ataxia, multiple sclerosis, nervous system dysfunction, memory lapse, epilepsy, encephalitis, prion disease, and neuropathy.

In an embodiment, the diseases of brain and nervous system may be a cerebrovascular disease. Cerebrovascular disease may refer to a condition that the cerebral blood vessels, through which blood is supplied to the brain tissue, are blocked or burst, causing damage to the topical brain tissue. In an embodiment, the cerebrovascular disease may be one or more selected from ischemic stroke, hemorrhagic stroke, cerebral infarction, cerebral vein thrombosis, arteritis, vascular dementia, myocardial infarction, and angina.

The ischemic brain disease may be a transient ischemic attack, a macrovascular disease, an arteriosclerotic lesion, a psychogenic embolism, or a thermocollinear stroke.

The host cells may be HEK-293E cells, Chinese hamster ovary (CHO) cells, baby hamster kidney (BHK) cells, NIH-3T3 cells, HEK-293T cells, or COS-7 cells.

The vector may be linear DNA, plasmid DNA, or recombinant viral vector, and the recombinant virus may be selected from retrovirus, adenovirus, adeno-associated virus, herpes simplex virus, and lentivirus.

The term "prevention" refers to any action that suppresses or delays the onset of degenerative brain disease-related diseases by administration of the pharmaceutical composition according to the present disclosure.

The term "treatment" refers to any action in which symptoms for a degenerative brain disease-related disease are improved or advantageously changed by administration of the pharmaceutical composition according to the present disclosure.

The therapeutically effective amount of the composition may vary depending on various factors, for example, the administration method, the target site, the patient's condition, and the like. Therefore, when used in the human body, the dosage may be adjusted to be at an appropriate level in consideration of safety and efficiency. It is also possible to estimate the amount used in humans from the effective amount determined through animal experiments. These considerations which need to be taken into when the effective amount is determined, are described in for example, Hardman and Limbird, eds., Goodman and Gilman's The Pharmacological Basis of Therapeutics, 10th ed.(2001), Pergamon Press; and E. W. Martin ed., Remington's Pharmaceutical Sciences, 18th ed. (1990), Mack Publishing Co.

The composition may include carriers, diluents, excipients, or a combination of two or more of these, which are commonly used in biological preparations. A pharmaceutically acceptable carrier is not particularly limited as long as it is suitable for delivery of the composition in vivo, and, for example, compounds described in Merck Index, 13th ed., Merck & Co. Inc., saline, sterilized water, Ringer's solution, buffered saline, dextrose solution, maltodextrin solution, glycerol, ethanol, and a combination of one or more of these components may be used, and if needed, other additives, such as antioxidants, buffers, bacteriostatic agents, etc. may be further included.

In addition, a diluent, a dispersant, a surfactant, a binder, and a lubricant may be additionally added to make formulation into an injectable formulation, such as an aqueous solution, suspension, emulsion, or the like, pills, capsules, granules, or tablets. Further, the formulation may be made according to each disease or component by an appropriate method in the art or by using a method disclosed in Remington's Pharmaceutical Science (Mack Publishing Company, Easton Pa., 18th, 1990).

The composition may further include one or more types of active ingredients exhibiting the same or similar functions. The composition may include, based on the total weight of the composition, 0.0001% to 10 wt % of the protein, or 0.001% to 1 wt % of the protein.

The composition may be administered parenterally (for example, intravenously, subcutaneously, intraperitoneally, or topically applied) or orally, according to a target method, and the dosage may vary depending on the patient's weight, age, sex, health status, diet, the administration time, the administration method, the excretion rate, and severity of disease. The daily dosage of the composition may be from 0.0001 mg/ml to 10 mg/ml, or 0.0001 mg/ml to 5 mg/ml, and may be administered once to several times a day.

In the case of a vector containing a polynucleotide encoding the peptide, the amount thereof may be from 0.05 mg to 500 mg, or 0.1 mg to 300 mg. In the case of a recombinant virus containing a polynucleotide encoding the peptide of the present disclosure, the amount thereof may be from $10^3$ IU to $10^{12}$ IU (10 to $10^{10}$ PFU), or $10^5$ to $10^{10}$ IU. However, these amounts are not limited thereto.

In addition, in the case of a cell containing a polynucleotide encoding the peptide, the number of cells may be from $10^3$ to $10^8$, from $10^4$ to $10^8$, from $10^3$ to $10^7$, or from $10^4$ to $10^7$.

In addition, the effective dosage of the composition containing the vector or cell containing the polynucleotide encoding the peptide as an active ingredient may be as follows, per 1 kg of body weight: in the case of a vector, from 0.05 mg/kg to 12.5 mg/kg; in the case of a recombinant virus, from $10^7$ to $10^{11}$ virus particles ($10^5$ to $10^9$ IU)/kg; and in the case of cells, from $10^3$ cells/kg to $10^6$ cells/kg, and for example, in the case of a vector, from 0.1 mg/kg to 10 mg/kg, in the case of a recombinant virus, from $10^8$ to $10^{10}$ particles ($10^6$ to $10^8$ IU)/Kg, and in the case of cells, from $10^2$ to $10^5$ cells/kg. The effective dosage of the composition may be administered 2 to 3 times a day. The composition as described above is not necessarily limited thereto, and may vary depending on the condition of the patient and the degree of onset of neurological diseases.

The composition may further include suitable carriers, excipients, and diluents which are commonly used in the preparation of pharmaceutical compositions. The composition may be administered parenterally, and when the parenteral administering is used, an injection method for external use of the skin or intraperitoneal injection, rectal injection, subcutaneous injection, intravenous injection, intramuscular injection, or intrathoracic injection may be selected, and is not limited thereto.

The compositions may be formulated and used in the form of external preparations, suppositories, and sterile injectable solutions according to conventional methods. Carriers, excipients, and diluents that may be included in the composition may include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oils. The formulation may be performed using diluents or excipients, such as fillers, extenders, binders, wetting agents, disintegrants, and surfactants which are usually used. Formulations for parenteral administration may include sterilized aqueous solutions, non-aqueous solutions, suspensions, emulsions, lyophilized formulations, and suppositories. As the non-aqueous solvent and suspending agent, propylene glycol, polyethylene glycol, vegetable oil such as olive oil, and injectable ester such as ethyl oleate may be used. As a base for suppositories, witepsol, macrogol, tween 61, cacao butter, laurin paper, glycerogelatin, and the like may be used.

The dosage of the composition varies depending on the condition and weight of the patient, the severity of the disease, the form of the drug, the route and duration of administration, but may be appropriately selected by those skilled in the art. However, to obtain suitable effects, the composition may be administered at 0.0001 g/kg to 1 g/kg per day, or 0.001 mg/kg to 200 mg/kg, but the dosage thereof is not limited thereto. The dosage may be administered in the bolus form or may be divided into several portions, which are then administered separately a day. The dosage does not limit the scope of the present disclosure.

Another aspect provides a health functional food for preventing or alleviating diseases of brain and nervous system, the health functional food containing, as an active ingredient, a peptide including any one amino acid sequence selected from SEQ ID NOs: 1 to 3, at least one polynucleotide encoding the peptide, a vector containing the polynucleotide, or a host cell containing the vector.

The diseases of brain and nervous system is the same as described above.

The term "improvement" used herein refers to any action that at least reduces a parameter associated with an abnormal condition, for example, the severity of a symptom. In this regard, the health functional food composition may be used before or after the onset stage of the disease in order to prevent or alleviate the diseases of brain and nervous system, simultaneously or separately from the drug for treatment.

In the case of the food composition, an active ingredient may be added as it is or used with other foods or food ingredients, and may be appropriately used according to a conventional method. The mixing amount of the active ingredient may be appropriately determined depending on the purpose of use (for prevention or alleviation). In general, in the preparation of food or beverage, the composition according to the present disclosure may be added in an amount of 60 wt % or less, or 40 wt % or less, based on the raw material thereof. However, in the case of long-term intake for the purpose of health and hygiene or for the purpose of health control, the upper limit of the amount may be less than 60 wt % or less.

In addition to containing the active ingredient as an essential ingredient in the indicated ratio, the food composition may further include other ingredients, which are not limited. In an embodiment, like those used in ordinary beverages, various flavoring agents or natural carbohydrates may be included as additional ingredients. Examples of the natural carbohydrates include: monosaccharides such as glucose, fructose, and the like; disaccharides such as maltose, sucrose, and the like; polysaccharides, for example, common sugars such as dextrin and cyclodextrin; and sugar alcohols such as xylitol, sorbitol, and erythritol. As flavoring agents other than those described above, natural flavoring agents (taumatin, and stevia extract (for example, rebaudioside A, glycyrrhizin, etc.)) and synthetic flavoring agents (saccharin, aspartame, etc.) may be used. The proportion of the natural carbohydrate may be appropriately determined by a person skilled in the art.

Besides, the food composition may include various nutrients, vitamins, minerals (electrolytes), flavoring agents such as synthetic flavoring agents and natural flavoring agents, coloring agents and flavorenhancer (cheese, chocolate, etc.), pectic acid and its salts, alginic acid and salts, organic acids, protective colloidal thickeners, pH adjusters, stabilizers, preservatives, glycerin, alcohols, carbonates used in carbonated beverages, and the like. These ingredients may be used independently or in combination. The proportion of these additives may also be appropriately selected by a person skilled in the art.

The peptide according to an aspect may bind to erythropoietin receptors, inhibit cell death, and have no side effects of cell proliferation, so that the peptide may be usefully used in the prevention or treatment of diseases of brain and nervous system.

Another aspect provides a method of preventing or treating diseases of brain and nervous system, the method including administering, to a subject, a pharmaceutical composition containing, as an active ingredient, a therapeutically effective amount of a peptide including any one amino acid sequence selected from SEQ ID NOs: 1 to 3, at least one polynucleotide encoding the peptide, a vector containing the polynucleotide, or a host cell containing the vector.

Among the terms or elements described in the description of the pharmaceutical composition, the same as those already described are as described above.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 1A shows an image showing the structure of erythropoietin and FIG. 1B shows a comparison of the peptide of an aspect and the peptide sequence of erythropoietin;

FIG. 4A shows a graph of cell viability, FIG. 4B shows a graph of ROS, and FIG. 4C shows a graph of cell death;

DETAILED DESCRIPTION

Figure 1A:
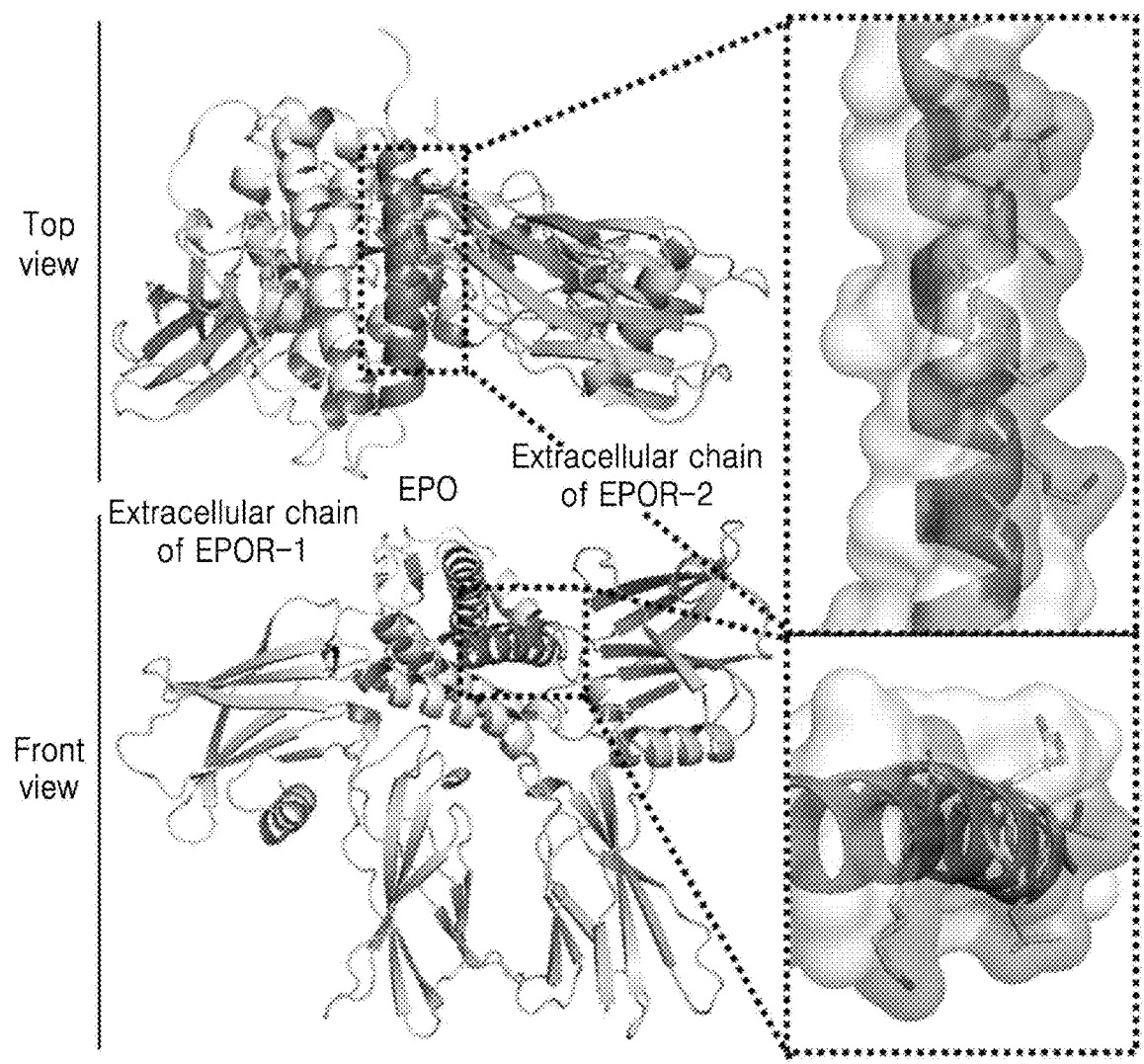

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, embodiment are presented to help the understanding of the present disclosure. However, the following examples are provided for easier understanding of the present disclosure, and the contents of the present disclosure are not limited by the following examples.

EXAMPLE

Example 1. Synthesis of Erythropoietin-Induced Peptide

The peptide of an aspect was synthesized as a monomer according to a conventionally known solid phase synthesis technology (Peptron, Daejeon, Korea).

Specifically, erythropoietin-induced peptides capable of binding to amino acid sequences (Arg103, Ser104, Leu105, Leu108, and Arg110) in the sequence of the target region (site 2) of the natural erythropoietin receptor were synthesized, and specific characteristics of each of the peptides were confirmed. A liquid chromatography/mass selective detector (HP 1100 series) was used to measure the concentration of the synthesized peptide. The measurement of purity was carried out by high performance liquid chromatography (SHIMADZU prominence HPLC) analysis (>95% purity).

FIG. 1 shows an image showing the structure of erythropoietin (left) and a comparison of the peptide of an aspect and the peptide sequence of erythropoietin (right).

As a result, as shown in FIG. 1 and Table 1, a novel synthetic peptide was able to be induced.

TABLE 1

| Peptide name | Sequence | Sequence number |
|---|---|---|
| SY-1 | LQLHVLKAVSGLRTLTTLLRALG | 1 |
| SY-2 | LQLHVLKAVSGLRTLTMIRRALG | 2 |
| SY-3 | LQLHVLKAVAGLRTLTMIRRALA | 3 |

For the peptide of an aspect, hydrophobicity, charge, and isoelectric point (pi) were calculated, and are shown in Table 2.

Experimental Examples

1. Confirmation of Binding Affinity of New Peptides

In order to confirm whether the erythropoietin-induced peptide prepared in Example 1 acts by binding to the erythropoietin receptor having a target region, the binding strength was confirmed using a surface plasmon resonance (SPR) technique. The SPR technique uses an optical principle to measure the interaction between biomolecules in real time without a specific label, and is a system that analyzes the affinity and kinetics between two molecules, that is, Ka (association rate) and Kd (dissociation rate).

Specifically, the real-time SPR analysis was performed using Reichert SPR Biosensor SR 7500C equipment (Reichert Inc., NY, USA). Receptor mouse EPOR chimera protein (Soluble mouse EPOR chimera protein)(R&D Systems, Minneapolis, Minn., USA) was covalently bonded to a chip (BR-1005-39, Pharmacia Biosensor AB) coated with carboxy methylated dextran matrix by an amine coupling procedure using an amine coupling kit (BR-1000-50, GE Healthcare, USA) according to the manufacturer's manual. Peptides having concentrations of 5, 2.5 and 1.25 μM according to the present disclosure and scrambled peptides were tested by flowing at a flow rate of 5 μl/minute. In addition, the experiment was independently repeated to increase the accuracy. In addition, DMSO was flowed at 5 μl/minute to normalize the signal. After sufficiently inducing the binding of the peptide of an aspect to the receptor, regeneration was induced by injecting 20 μl/minute of 25 mM acetic acid into a sensor chip.

Figure 2:
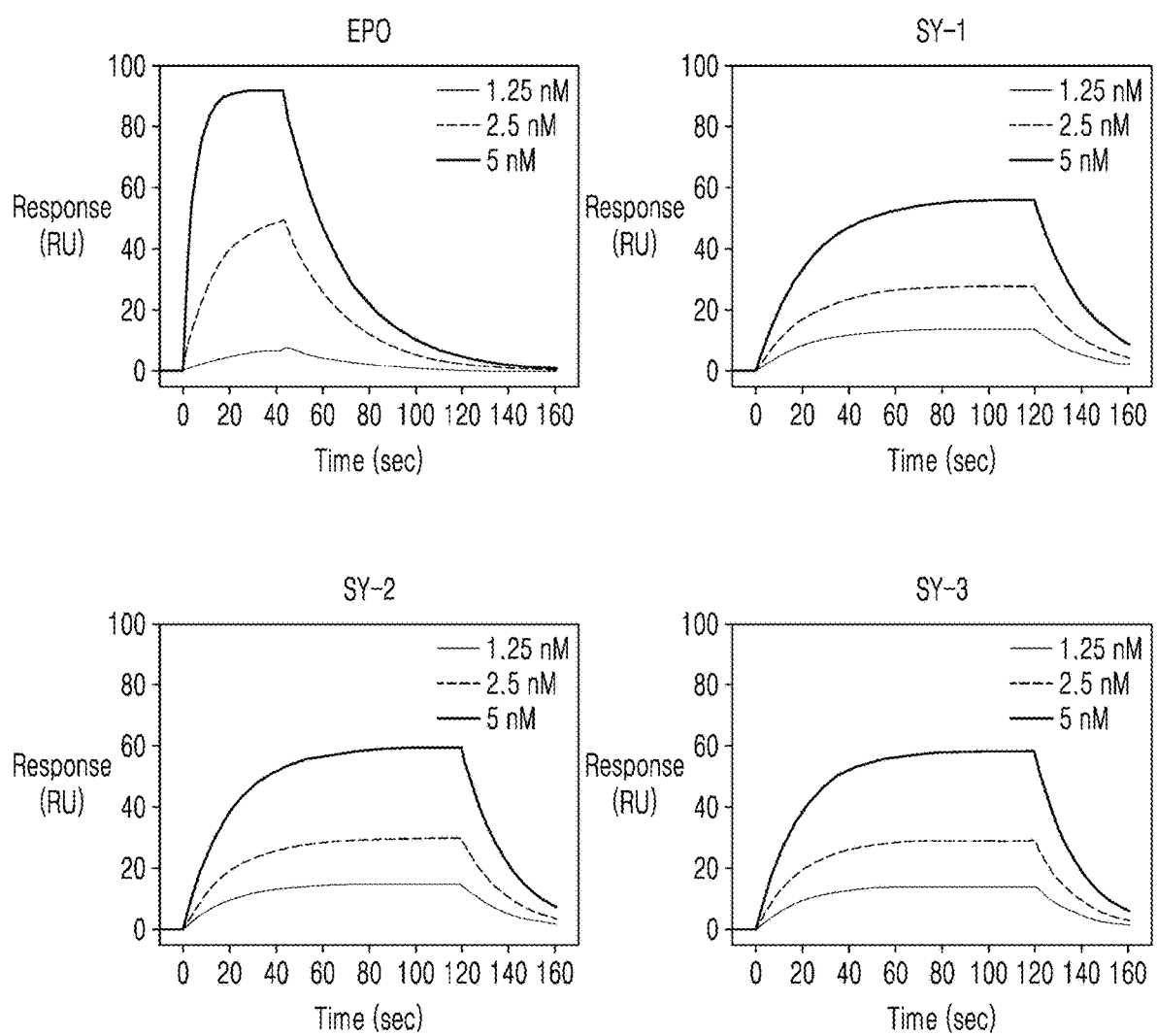
FIG. 2 shows a graph showing the binding affinity of a peptide of an aspect to an erythropoietin receptor compared with a control group.

FIG. 2 shows a graph showing the binding affinity of a peptide of an aspect to an erythropoietin receptor compared with a control group.

As a result, as shown in FIG. 2, it was confirmed that the result value increased in proportion to the concentration of the erythropoietin-induced peptide of an embodiment. This suggests that the peptide of an aspect binds to the target

TABLE 2

| Peptide | Amino acid | Netcharge (at pH7.0) | Hydrophobicity (%) | MW | Theoretical pI | Instability index | Aliphatic index | GRAVY index | Target | Extinction coefficients ($M^{-1}cm^{-1}$) |
|---|---|---|---|---|---|---|---|---|---|---|
| SY-1 | 23 | 3.1 | 52.17% | 2474.03 | 12.01 | 36.80 (stable) | 169.57 | 0.83 | 91-113 amino acid in human EPO | 0 |
| SY-2 | 23 | 4.1 | 52.17% | 2547.15 | 12.3 | 53.33 (unstable) | 152.61 | 0.613 | 91 to 113 amino acid in human EPO | 0 |
| SY-3 | 23 | 4.1 | 60.87% | 2545.17 | 12.3 | 53.33 (unstable) | 161.3 | 0.822 | 91 to 113 amino acid in human EPO | 0 | portion of the erythropoietin receptor. In addition, as shown in Table 3, the erythropoietin-induced peptide of an embodiment appears similar to or slightly greater than the previously known binding affinity (up to 1 µM).

TABLE 3

| SY-1 | ka | kd | KD = Kd/Ka |
|---|---|---|---|
|  | 31.5970 | 0.0446 | 1.41061 mM |
| SY-2 | ka | kd | KD |
|  | 32.5770 | 0.0506 | 1.55398 mM |
| SY-3 | ka | kd | KD |
|  | 25.6240 | 0.0554 | 2.16266 mM |

That is, it can be seen that the binding affinity of the peptide according to an embodiment with respect to the erythropoietin receptor, has a KD value of 0.6 mM to 3.0 mM, for example, 1.41061 mM, 1.55398 mM, and 2.16266 mM.

2. Confirmation of the Cytoprotective Effect of New Peptides 2.1 Confirmation of Cell Viability in Stressful Situations To confirm whether the peptide of Example 1 exhibits a cytoprotective effect, cell viability was confirmed in a stress situation in which an increase in reactive oxygen was induced with hydrogen peroxide ($H_2O_2$).

Specifically, cell viability was evaluated using MTS analysis (CellTiter 96 Aqueous One Solution Cell Proliferation Assay, Promega, Madison, Wis., USA). PC12 cells were seeded into a 96 well plate ($5 \times 10^4$ cells per well/), and an increase in reactive oxygen was induced with 300 µM hydrogen peroxide ($H_2O_2$). Next, 0.5 IU/ml of an erythropoietin compound, and a peptide of an aspect were added, separately, and then 20 µl of MTS solution was added to each well, followed by waiting for 3 hours. Next, the absorbance of each well of the 96-well plate was recorded using VERSA MAX at a wavelength of 490 nm to compare the initial cell number (0 hour) and the cell number after 48 hours.

Figure 3:
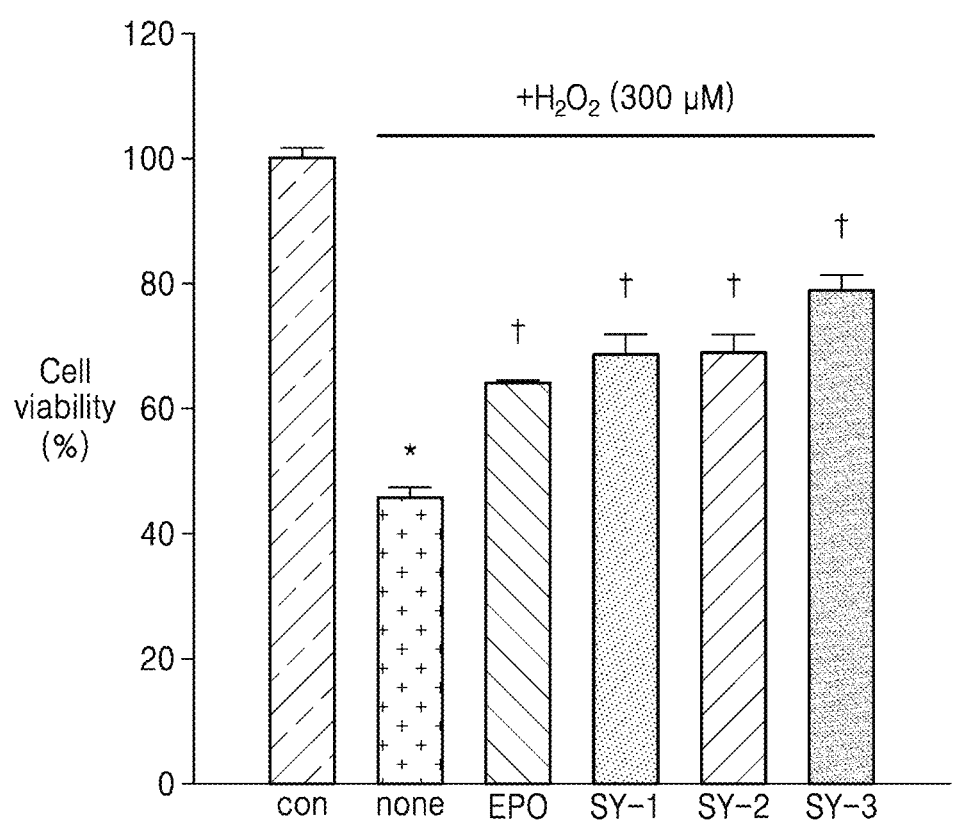
FIG. 3 is a graph showing cell viability in a stress situation of a peptide of an aspect; con is a negative control without any treatment; none is a cell which is exposed to stress situation only; EPO is an experimental group treated with erythropoietin; and SY-1, SY-2, and SY-3 are experimental groups treated with peptides of SEQ ID NOs 1 to 3, respectively.

FIG. 3 is a graph showing cell viability in a stress situation of a peptide of an aspect; con is a negative control without any treatment; none is a cell which is exposed to stress situation only; EPO is an experimental group treated with erythropoietin; and SY-1, SY-2, and SY-3 are experimental groups treated with peptides of SEQ ID NOs 1 to 3, respectively.

As a result, as shown in FIG. 3, it was confirmed that the peptide of an aspect protects cells from apoptosis due to an increase in active oxygen. This shows that the peptide of an aspect exhibits a remarkable cell protective effect compared to when treated with a natural erythropoietin compound.

2.2 Confirmation of Cell Viability in Hypoxic Environment

Cell viability, reactive oxygen species (ROS), and cell death (TUNEL) were evaluated to confirm whether the produced peptide exhibits a protective effect on cells in a hypoxic environment (H/R condition).

First, the degree of cell viability was confirmed. Specifically, HT-22 cells cultured on a 96-well plate or a 6-well plate for 24 hours were maintained under hypoxic condition for 18 hours in a sealed airtight container of Anaeropack (Mitsubishi Gas Company, Tokyo, Japan). The Anaeropack absorbs oxygen and generates carbon dioxide, thereby inducing a hypoxic environment. Next, reoxygenation was performed at 5% $CO_2$ and 37° C. for 3 hours. Next, after 19 hours of treatment with EPO or a peptide of an aspect in the hypoxic environment, cell viability assays were performed.

Figure 4A:
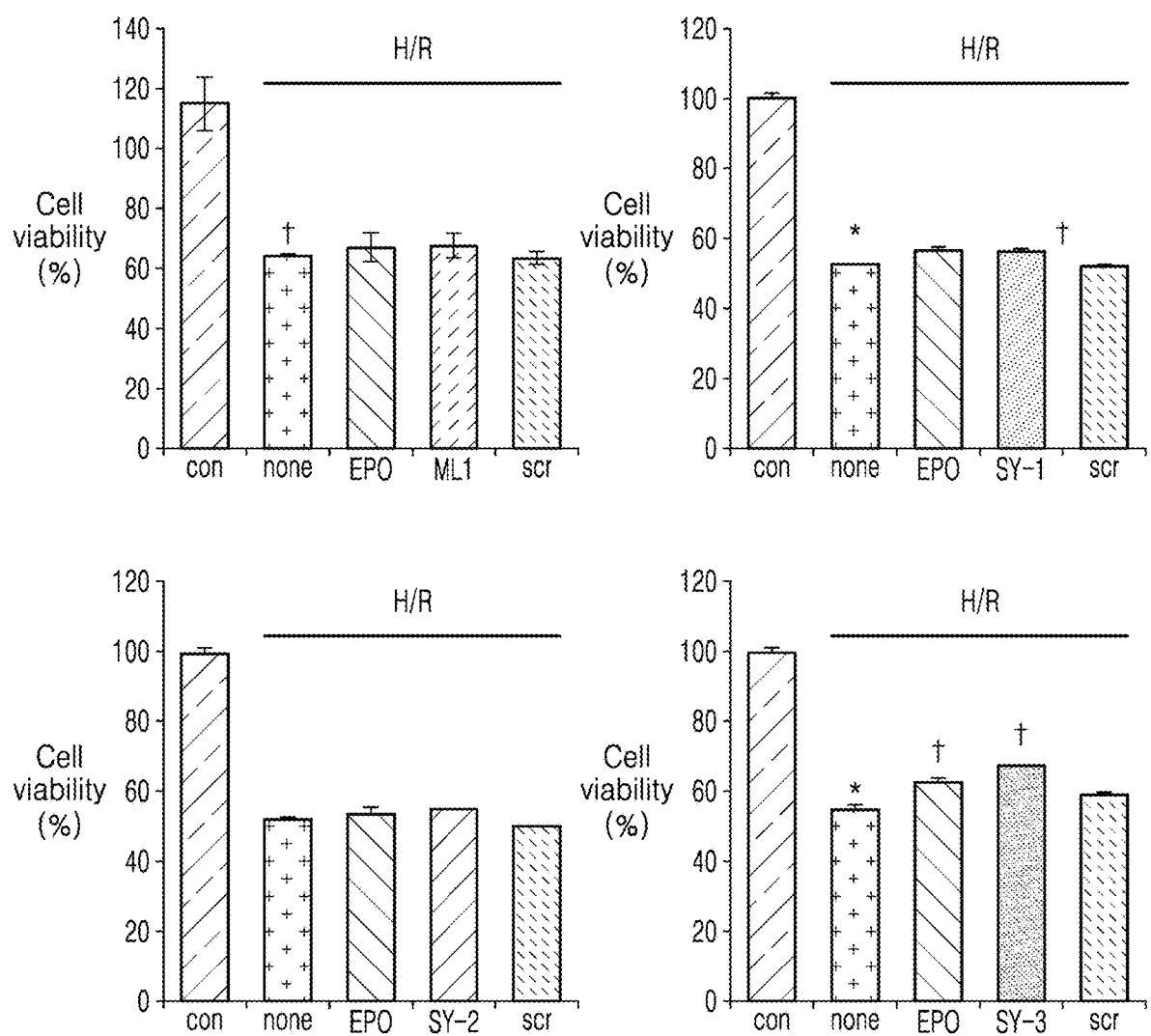
FIG. 4A-4C show graphs of cell viability, reactive oxygen species (ROS), and cell death (TUNEL) in a hypoxic environment (H/R condition) of the peptide of an aspect.
Figure 4B:
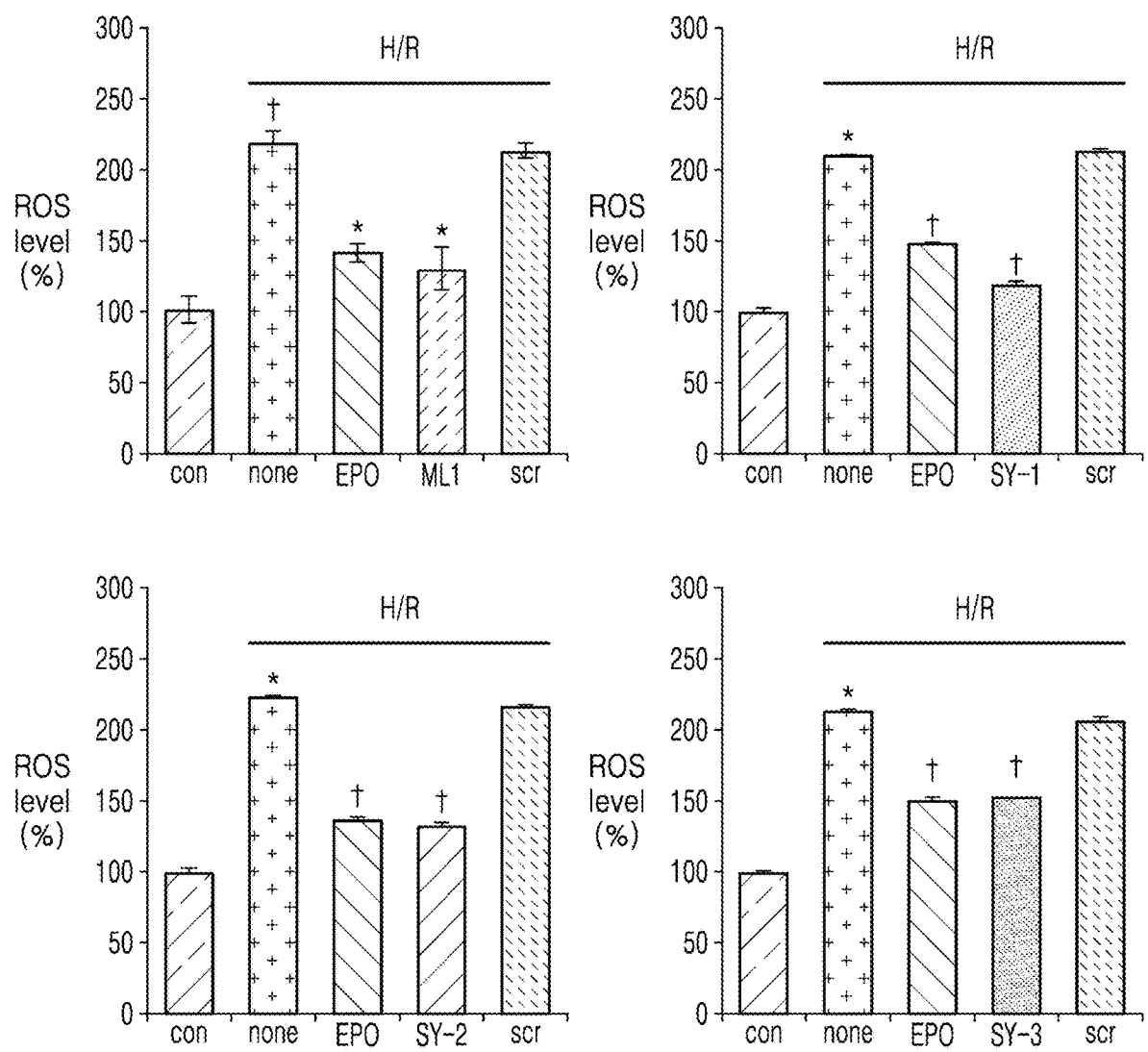
Figure 4C:
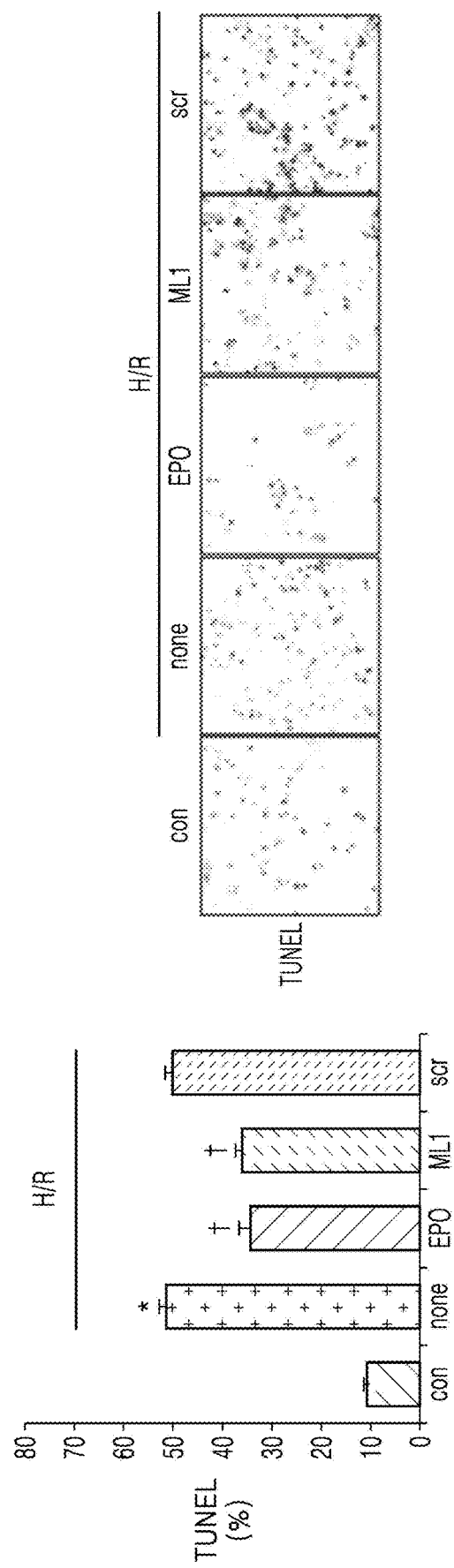

FIG. 4 shows graphs of cell viability, reactive oxygen species (ROS), and cell death (TUNEL) in a hypoxic environment (H/R condition) of the peptide of an aspect: A shows a graph of cell viability, B shows a graph of ROS, and C shows a graph of cell death.

As a result, as shown in FIG. 4, it was confirmed that the peptide of an aspect protects cells from apoptosis due to H/R condition. In addition, it can be seen that this effect is remarkable compared to the cell protective effect obtained by treatment with a natural erythropoietin compound.

Next, intracellular ROS was measured.

Specifically, HT22 cells were seeded into each well of a 96-well plat and cultured for 24 hours. After treatment with erythropoietin and the peptide of an aspect according to the conditions of each group, 5 µM of CM-H2DCFDA was added and an additional culture was performed for 30 minutes. Next, after removing residual H2DCFDA that did not bind to ROS by using PBS, the fluorescence intensity of DCF was measured at 488 nm/525 nm (ex/em) by using a fluorescent plate reader.

As a result, as shown in FIG. 4, it was confirmed that the prepared peptide protects cells from ROS caused by H/R conditions. In addition, it can be seen that this effect is remarkable compared to the cell protective effect obtained by treatment with a natural erythropoietin compound.

Next, cell death (TUNEL) was measured.

Specifically, the culture solution was first removed, washing was performed three times with phosphate-buffered saline (PBS), and then, the cells were immobilized with 4% PFA for 10 minutes at room temperature. Next, after washing twice with PBS for 5 minutes, proteinase K (20 µg/ml) was instilled and the cells were incubated for 10 minutes at 37° C. After washing, 1% $H_2O_2$ (in PBS) was reacted at room temperature for 5 minutes, washing was performed using PBS, 75 µl of equilibration buffer was instilled, and then, the reaction was carried out for 10 seconds, and then the equilibration buffer was removed. Next, after instilling 55 µl/5 $cm^2$ of working strength TdT (terminal deoxynucleotidyl transferase) enzyme, the reaction was caused for 1 hour while humidity was maintained at 37° C., and a working strength stop/wash buffer was added thereto and a reaction was used at room temperature for 10 minutes. After washing with PBS, 65 µl/5 $cm^2$ of anti-digoxigenin peroxidase was instilled and a reaction was caused at room temperature for 30 minutes while humidity was maintained constant. Finally, after washing with PBS, a reaction was caused with a mixed solution including 0.02% 3,3-diaminobenzidine tetrahydrochloride (DAB), which is a coloring agent, and 0.003% $H_2O_2$ at room temperature for 10 minutes, and then the result was observed with an optical microscope.

As a result, as shown in FIG. 4, it was confirmed that the peptide of an aspect protects cells from apoptosis due to H/R condition.

2.3 Comparison of Cell Viability of Peptides in Hypoxic Environment

Cell viability was compared when treated with SY-1, SY-2 and SY-3 of H/R cells cultured under low oxygen conditions (Hypoxia) and later cultured under oxygen conditions (Reoxygenation).

Figure 5:
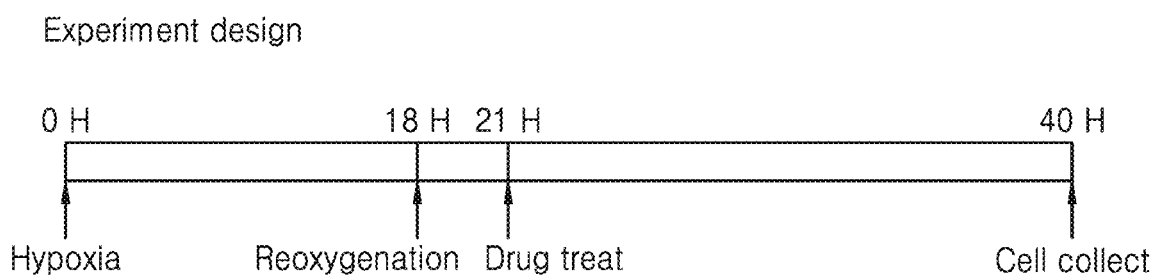
FIG. 5 shows a schematic diagram of a hypoxia-reoxygenation experiment.

FIG. 5 shows a schematic diagram of a hypoxia-reoxygenation experiment.

As shown in FIG. 5, the hypoxic step was performed on the cells for 18 hours, and then reoxygenation was performed for 3 hours. Thereafter, 19 hours after the treatments with peptides of an aspect SY-1, SY-2, and SY-3 and control groups EPO, ML1, and ML1-1, a reaction was identified. At this time, the concentration of EPO was 0.4 IU.

Figure 6:
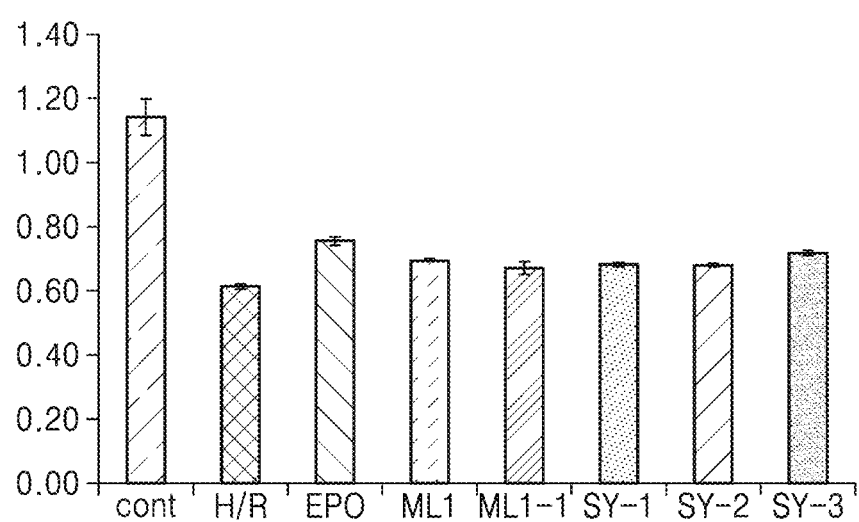
FIG. 6 shows a graph showing cell viability under hypoxia-reoxygenation conditions when treated with the peptide of an aspect.

FIG. 6 shows a graph showing cell viability under hypoxia-reoxygenation conditions when treated with the peptide of an aspect.

Figure 7:
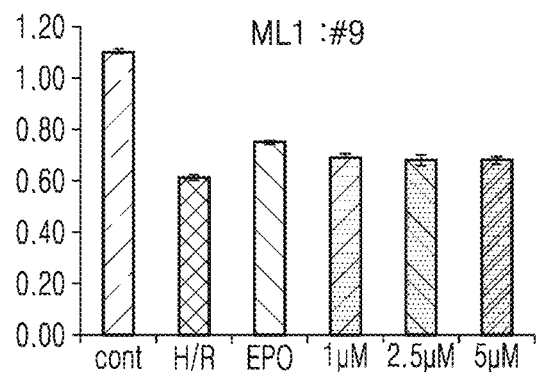
FIG. 7 shows a graph of cell viability according to concentrations under hypoxia-reoxygenation conditions when treated with the peptide of an aspect.
Figure 7:
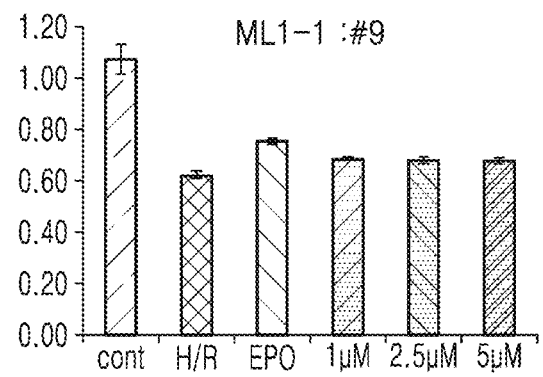
Figure 7:
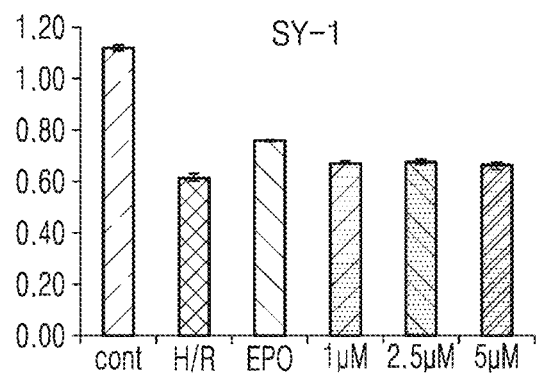
Figure 7:
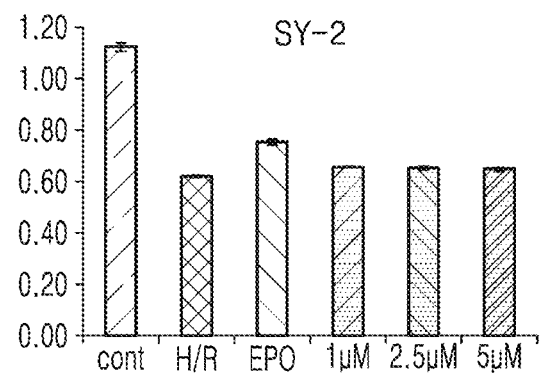
Figure 7:
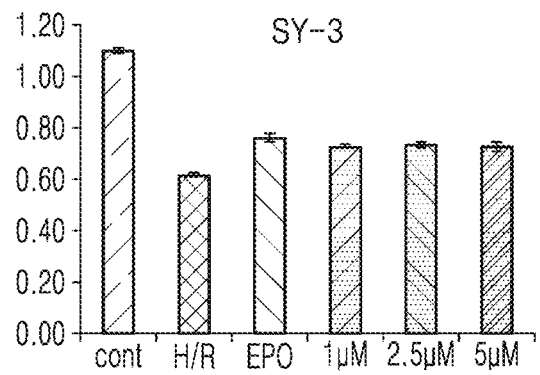

FIG. 7 shows a graph of cell viability according to concentrations under hypoxia-reoxygenation conditions when treated with the peptide of an aspect.

Table 4 show cell viability under hypoxia-reoxygenation conditions according to concentrations.

TABLE 4

| ML1 (#1) | cont | H/R | EPO | 1 uM | 2.5 uM | 5 uM |
|---|---|---|---|---|---|---|
|  | 1.123 | 0.628 | 0.745 | 0.705 | 0.662 | 0.698 |
|  | 1.106 | 0.611 | 0.761 | 0.673 | 0.693 | 0.671 |
|  | 1.109 | 0.614 | 0.755 | 0.696 | 0.696 | 0.682 |
| Average | 1.113 | 0.618 | 0.754 | 0.691 | 0.684 | 0.684 |
| STDEV | 0.009 | 0.009 | 0.008 | 0.017 | 0.019 | 0.014 |
| ML1-1 (#9) | cont | H/R | EPO | 1 uM | 2.5 uM | 5 uM |
|  | 1.114 | 0.638 | 0.747 | 0.694 | 0.673 | 0.681 |
|  | 1.109 | 0.622 | 0.759 | 0.668 | 0.696 | 0.688 |
|  | 1.008 | 0.611 | 0.764 | 0.689 | 0.675 | 0.665 |
| Average | 1.077 | 0.624 | 0.757 | 0.684 | 0.681 | 0.678 |
| STDEV | 0.060 | 0.014 | 0.009 | 0.014 | 0.013 | 0.012 |
| SY-1 | cont | H/R | EPO | 1 uM | 2.5 uM | 5 uM |
|  | 1.135 | 0.627 | 0.745 | 0.662 | 0.649 | 0.648 |
|  | 1.112 | 0.616 | 0.761 | 0.657 | 0.663 | 0.653 |
|  | 1.126 | 0.619 | 0.765 | 0.644 | 0.652 | 0.641 |
| Average | 1.124 | 0.621 | 0.757 | 0.654 | 0.655 | 0.647 |
| STDEV | 0.012 | 0.006 | 0.011 | 0.009 | 0.007 | 0.006 |
| SY-2 | cont | H/R | EPO | 1 uM | 2.5 uM | 5 uM |
|  | 1.125 | 0.631 | 0.758 | 0.658 | 0.671 | 0.652 |
|  | 1.109 | 0.604 | 0.763 | 0.673 | 0.667 | 0.677 |
|  | 1.122 | 0.614 | 0.761 | 0.682 | 0.689 | 0.655 |
| Average | 1.119 | 0.616 | 0.761 | 0.671 | 0.676 | 0.661 |
| STDEV | 0.009 | 0.014 | 0.003 | 0.012 | 0.012 | 0.014 |
| SY-3 | cont | H/R | EPO | 1 uM | 2.5 uM | 5 uM |
|  | 1.113 | 0.628 | 0.747 | 0.722 | 0.739 | 0.707 |
|  | 1.101 | 0.611 | 0.776 | 0.736 | 0.741 | 0.732 |
|  | 1.092 | 0.614 | 0.763 | 0.719 | 0.724 | 0.741 |
| average | 1.102 | 0.618 | 0.762 | 0.726 | 0.735 | 0.727 |
| STDEV | 0.011 | 0.009 | 0.015 | 0.009 | 0.009 | 0.018 |

As a result, as shown in FIGS. 5 to 7 and Table 4, it was confirmed that the cell viability was higher when treated with the peptide of an aspect than treated with the control groups, and when treated with SY-3, the cell viability was the highest.

Next, the expression levels of the apoptosis-related proteins Caspase-9, Caspase-3, Bax, and β-actin of the cells (H/R cells) were measured using Western blot and compared.

Figure 8:
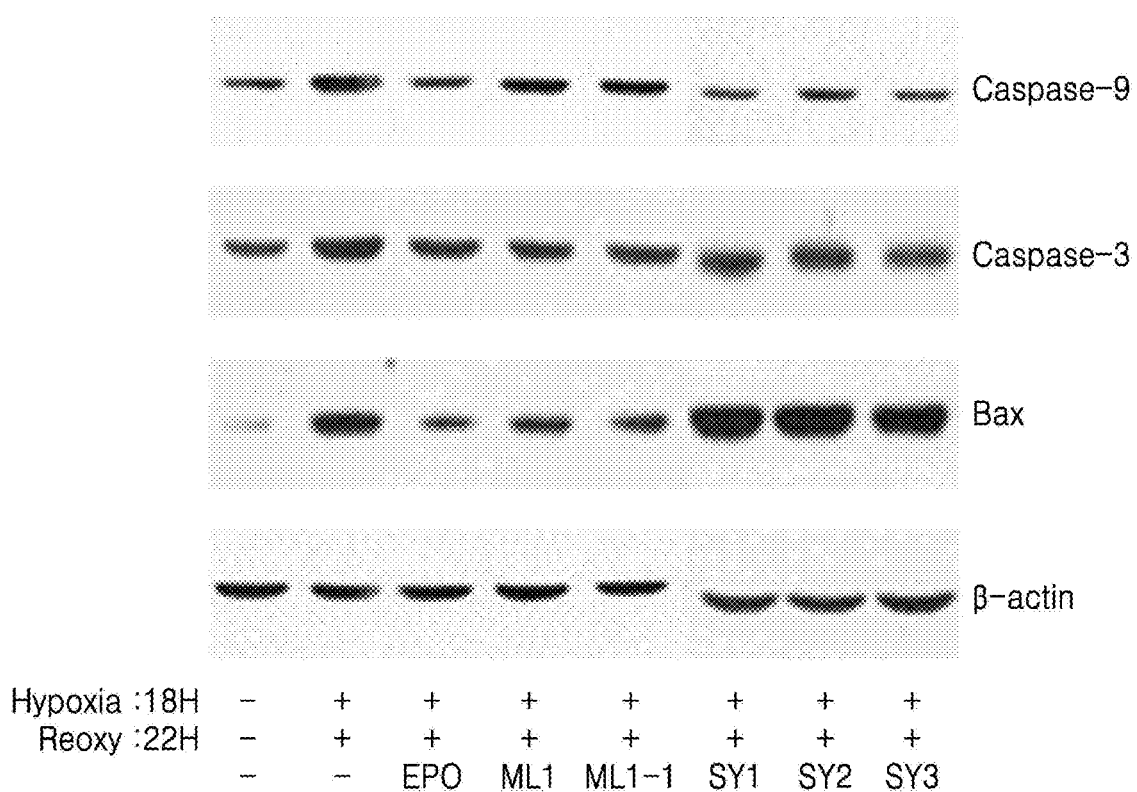
FIG. 8 shows a graph showing the expression of apoptosis-related proteins under hypoxia-reoxygenation conditions when treated with the peptide of an aspect.

FIG. 8 shows a graph showing the expression of apoptosis-related proteins under hypoxia-reoxygenation conditions when treated with the peptide of an aspect.

Figure 9:
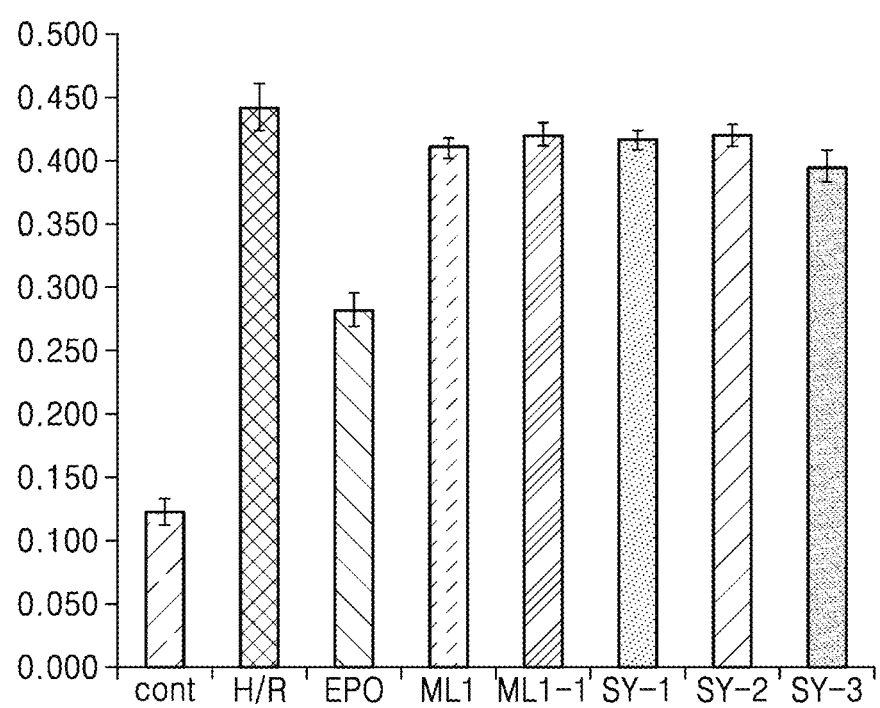
FIG. 9 shows a graph showing Caspase-9 activity under hypoxia-reoxygenation conditions when treated with the peptide of an aspect.

FIG. 9 shows a graph showing Caspase-9 activity under hypoxia-reoxygenation conditions when treated with the peptide of an aspect.

As a result, as shown in FIGS. 8 and 9, the expression of the apoptosis-related proteins Caspase-9, Caspase-3, Bax and β-actin was lower when treated with the peptide of an aspect than when treated with the control groups, and in particular, when treated with SY-3, the cell viability was the highest.

4. Confirmation of Cell Proliferation Inhibitory Effect of New Peptide

Side effects such as cell proliferation of the three peptides SY-1, SY-2 and SY-3 prepared in Example 1 were confirmed.

Specifically, MTS analysis (CellTiter 96 Aqueous One Solution Cell Proliferation Assay, Promega, Madison, Wis., USA) method was used. PC12 cells were seeded into a 96 well plate ($5 \times 10^4$ cells per well), and then an erythropoietin compound and a peptide of an aspect were added thereto. Next, 20 µl of the MTS solution was added to each well and the cells were allowed to stand for 3 hours. Initial cell count (0 hours) and cell count after 48 hours were measured. Intracellular soluble formazan was determined by recording the absorbance of each well of the 96 well plate by using VERSA MAX at a wavelength of 490 nm.

Figure 10:
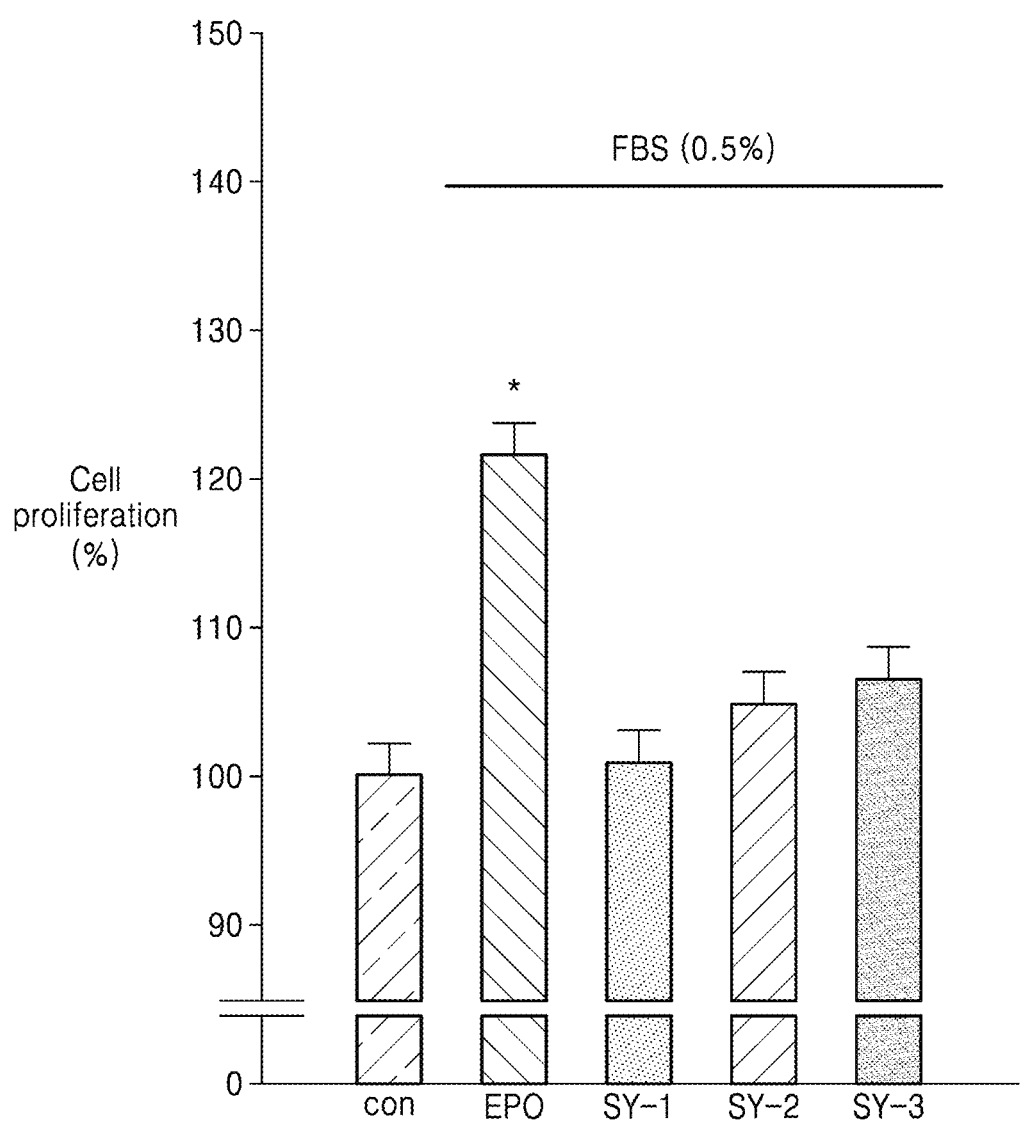
FIG. 10 shows a graph confirming the cell proliferation inhibitory effect of the peptide of an aspect: con is a negative control without any treatment; none is a cell which is exposed to stress situation only; EPO is an experimental group treated with erythropoietin; and SY-1, SY-2, and SY-3 are experimental groups treated with peptides of SEQ ID NOs 1 to 3, respectively.

As a result, as shown in FIG. 10, the cell proliferation rate of all of the peptides of an aspect was similar to those of the control groups, and as a result, it was confirmed that there were no cell-proliferation side effects.

4. Confirmation of Stroke Treatment and Brain Protection Effects of Novel Peptides in Animal Models 4.1 Preparation of Animal Models An MCAO animal model was prepared for use as the animal model used in this experiment.

First, a mouse was anesthetized with a mixture of 70% $N_2O$ and 30% $O_2$ and 3% isoflurane, and the anesthesia was maintained with 1.5 to 2.0% isofluorene. The neck skin of the experimental animal stably anesthetized was incised, and then, the bifurcation of the common carotid artery was exposed. The external carotid artery of the exposed part was tied and the internal carotid artery was carefully separated from the vagus nerve. Through the external carotid stump, the silicone coated 7-0 surgical nylon monofilament was pushed to the end of the middle cerebral artery (MCA) through the right internal carotid artery. Laser doppler flowmetry (perimed 5000 system, sweden) was used to determine whether focal cerebral ischemia was induced. During the operation, a heating pad (CMA 150, Stockholm, Sweden) was used to monitor the temperature of the rectum and the body temperature was maintained at 37±0.5° C. The nylon monofilament was maintained for 90 minutes, and then the monofilament structure was removed therefrom and re-perfusion was performed. Recovery of the clogged blood flow was confirmed using a laser Doppler flow meter. Next, for recovery after surgery, the mouse were recovered for 3 hours in a warm box at room temperature (30° C.). After the end of the re-perfusion time (24 hr. after reperfusion following 90 min MCAO), the brain was isolated by a humane method to obtain a brain tissue sample.

4.2 Confirmation of the Brain Protective Effect of the Novel Peptide

In order to confirm whether the peptide according to an aspect was effective in animal experiments as in cell experiments, 24 hours after damage to the brain of the animal model of 4.1, the animal model was cut off, and the brain was excised and washed with refrigerated physiological saline. Next, the washed brain was placed in a brain matrix (Stoelting Co, USA) and cut into 2 mm thickness by using a cutting knife to prepare a brain section. The prepared brain section was put in 15 ml of 0.125% TTC solution (62.5 mM Tris-HCl, 13 mM $MgCl_2$, 1.5% DMF), stained for 90 minutes at 37° C., washed with physiological saline, and imaged using a scanner. The obtained data was stored and analyzed on a computer.

Figure 11A:
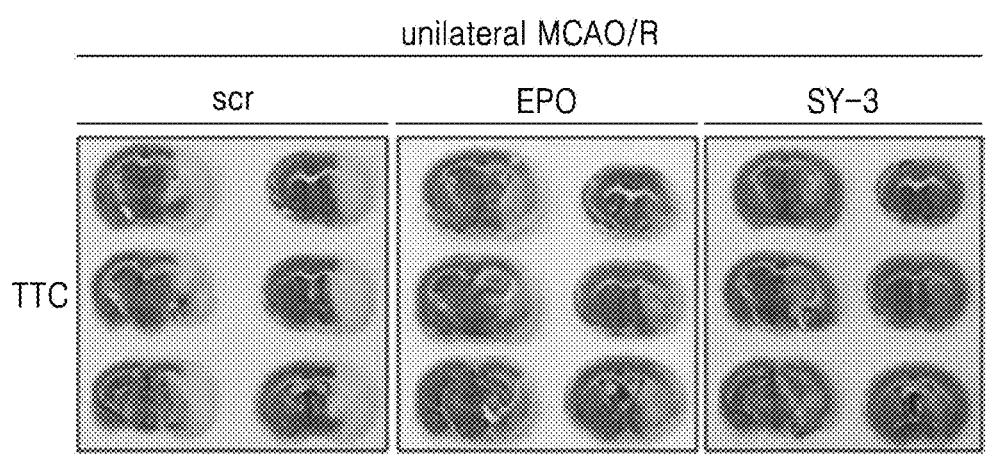
FIG. 11A is an image showing that a peptide of an aspect exhibits a cytoprotective effect in a stroke mouse model.
Figure 11B:
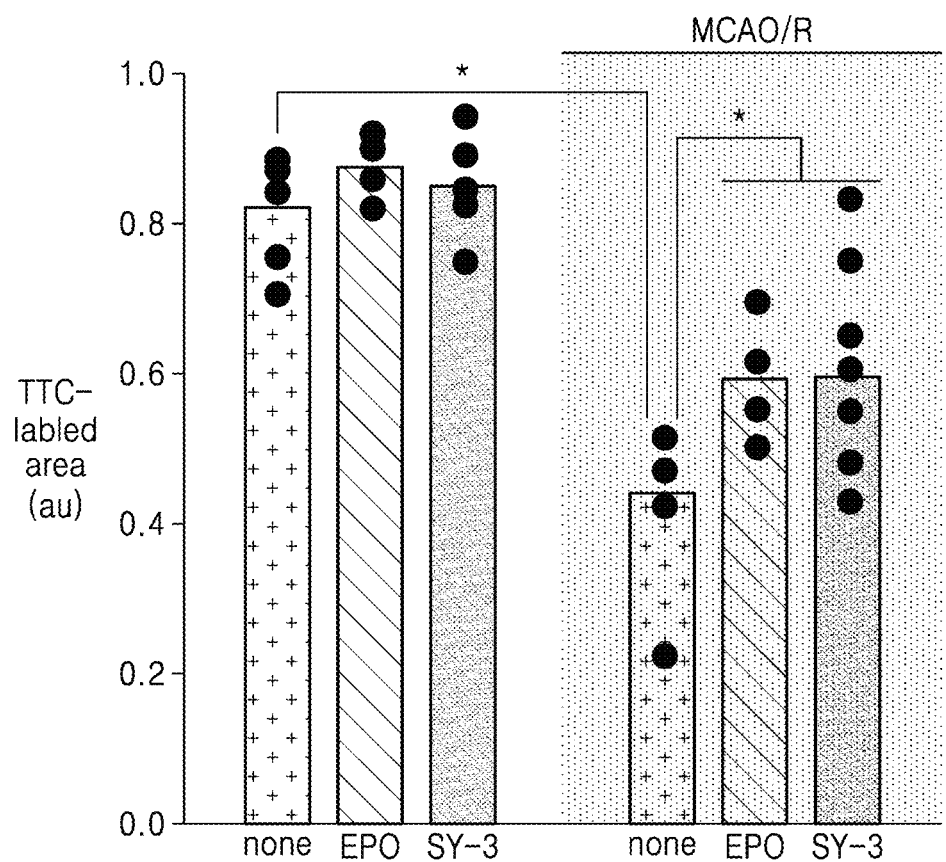
FIG. 11B is a graph showing the effect of stroke treatment in an animal model compared to a control group.

As a result, as shown in FIG. 11, it was confirmed that the peptide of an aspect has an effect of protecting the brain and treating a stroke in the mouse stroke model. In addition, in the case of the animal experiment, the effect of the new peptide compared to erythropoietin was much clearer than that of the cell experiment.

understood by those of ordinary skill in the art that various changes in form and details may be made therein without departing from the spirit and scope of the disclosure as defined by the following claims.

```
                              SEQUENCE LISTING

<160> NUMBER OF SEQ ID NOS: 3

<210> SEQ ID NO 1
<211> LENGTH: 23
<212> TYPE: PRT
<213> ORGANISM: Artificial Sequence
<220> FEATURE:
<223> OTHER INFORMATION: peptide of SY-1, SY-2, and SY-3

<400> SEQUENCE: 1

Leu Gln Leu His Val Leu Lys Ala Val Ser Gly Leu Arg Thr Leu Thr
1               5                   10                  15

Thr Leu Leu Arg Ala Leu Gly
            20

<210> SEQ ID NO 2
<211> LENGTH: 23
<212> TYPE: PRT
<213> ORGANISM: Artificial Sequence
<220> FEATURE:
<223> OTHER INFORMATION: peptide of SY-1, SY-2, and SY-3

<400> SEQUENCE: 2

Leu Gln Leu His Val Leu Lys Ala Val Ser Gly Leu Arg Thr Leu Thr
1               5                   10                  15

Met Ile Arg Arg Ala Leu Gly
            20

<210> SEQ ID NO 3
<211> LENGTH: 23
<212> TYPE: PRT
<213> ORGANISM: Artificial Sequence
<220> FEATURE:
<223> OTHER INFORMATION: peptide of SY-1, SY-2, and SY-3

<400> SEQUENCE: 3

Leu Gln Leu His Val Leu Lys Ala Val Ala Gly Leu Arg Thr Leu Thr
1               5                   10                  15

Met Ile Arg Arg Ala Leu Ala
            20
```

Peptides according to an aspect are easy to pass through a tissue-blood barrier, have excellent physiological activity in the protective activity of cells, and have an economic advantage due to low production costs. In addition, since there is no side effect of cell proliferation, a pharmaceutical composition containing a peptide of an aspect as an active ingredient can be usefully used in the treatment or prevention of cranial nervous system diseases.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be

What is claimed is:

1. A peptide consisting of an amino acid sequence of SEQ ID NO: 3.

2. The peptide of claim 1, wherein the peptide is capable of binding to an erythropoietin (EPO) receptor.

3. The peptide of claim 1, wherein the peptide exhibits a cytoprotective activity.

4. The peptide of claim 3, wherein the peptide has an activity of protecting neurons or brain cells.

5. The peptide of claim 1, wherein the peptide is a peptide that does not have cell-proliferation side effects.

6. A pharmaceutical composition for preventing or treating stroke, the pharmaceutical composition comprising as an active ingredient, the peptide of claim 1.

* * * * *